(12) United States Patent
Foster

(10) Patent No.: US 8,696,678 B2
(45) Date of Patent: Apr. 15, 2014

(54) MEDICAL TREATMENT MATERIAL DELIVERY APPARATUS

(75) Inventor: David Foster, Woodstock (GB)

(73) Assignee: Summit Medical Limited, Gloucestershire (GB)

(*) Notice: Subject to any disclaimer, the term of this patent is extended or adjusted under 35 U.S.C. 154(b) by 149 days.

(21) Appl. No.: 12/226,705

(22) PCT Filed: Apr. 25, 2007

(86) PCT No.: PCT/EP2007/003651
§ 371 (c)(1),
(2), (4) Date: Apr. 24, 2009

(87) PCT Pub. No.: WO2007/122006
PCT Pub. Date: Nov. 1, 2007

(65) Prior Publication Data
US 2010/0010495 A1    Jan. 14, 2010

(30) Foreign Application Priority Data
Apr. 26, 2006   (GB) .................................. 0608262.2

(51) Int. Cl.
*A61B 17/56* (2006.01)

(52) U.S. Cl.
USPC .................................. 606/93; 606/92; 606/94

(58) Field of Classification Search
USPC .............. 606/82–95; 604/61, 506, 69, 71, 62, 604/93.01, 124, 183–185, 218, 231, 232, 604/144, 156
See application file for complete search history.

(56) References Cited

U.S. PATENT DOCUMENTS

| | | | |
|---|---|---|---|
| 5,049,135 A * | 9/1991 | Davis ............................. | 604/181 |
| 5,106,370 A * | 4/1992 | Stewart ........................... | 604/61 |
| 5,298,023 A * | 3/1994 | Haber et al. .................... | 604/90 |
| 5,411,485 A * | 5/1995 | Tennican et al. ............... | 604/191 |
| 5,817,054 A * | 10/1998 | Grimm ........................... | 604/62 |
| 5,924,230 A * | 7/1999 | Hoke, Jr. ......................... | 42/60 |
| 6,047,861 A * | 4/2000 | Vidal et al. .................... | 222/137 |
| 6,428,463 B1 * | 8/2002 | Ravins et al. .................... | 600/7 |

FOREIGN PATENT DOCUMENTS

| | | |
|---|---|---|
| EP | 0 217 546 A | 4/1987 |
| GB | 2 126 482 A | 3/1984 |
| WO | WO95/20408 A | 8/1995 |

* cited by examiner

*Primary Examiner* — Nicholas Woodall
(74) *Attorney, Agent, or Firm* — Alix, Yale & Ristas, LLP

(57) ABSTRACT

A delivery apparatus for delivering material to a medical treatment site which comprises a plurality of containers for containing the material, a dispensing outlet and means for bringing each container into communication with the outlet and means for transferring material from the containers and through the outlet. The plurality of containers may be removably mounted within a removable cartridge. The apparatus is arranged so that the cartridge is biased to sequentially move each of the containers into communication with the outlet. The outlet may be provided at the end of a dispensing nozzle where the dispensing nozzle has an inner cross-sectional area that is uniform and the same as the containers so that no taper is provided as the material is dispensed from the containers and out of the outlet.

17 Claims, 11 Drawing Sheets

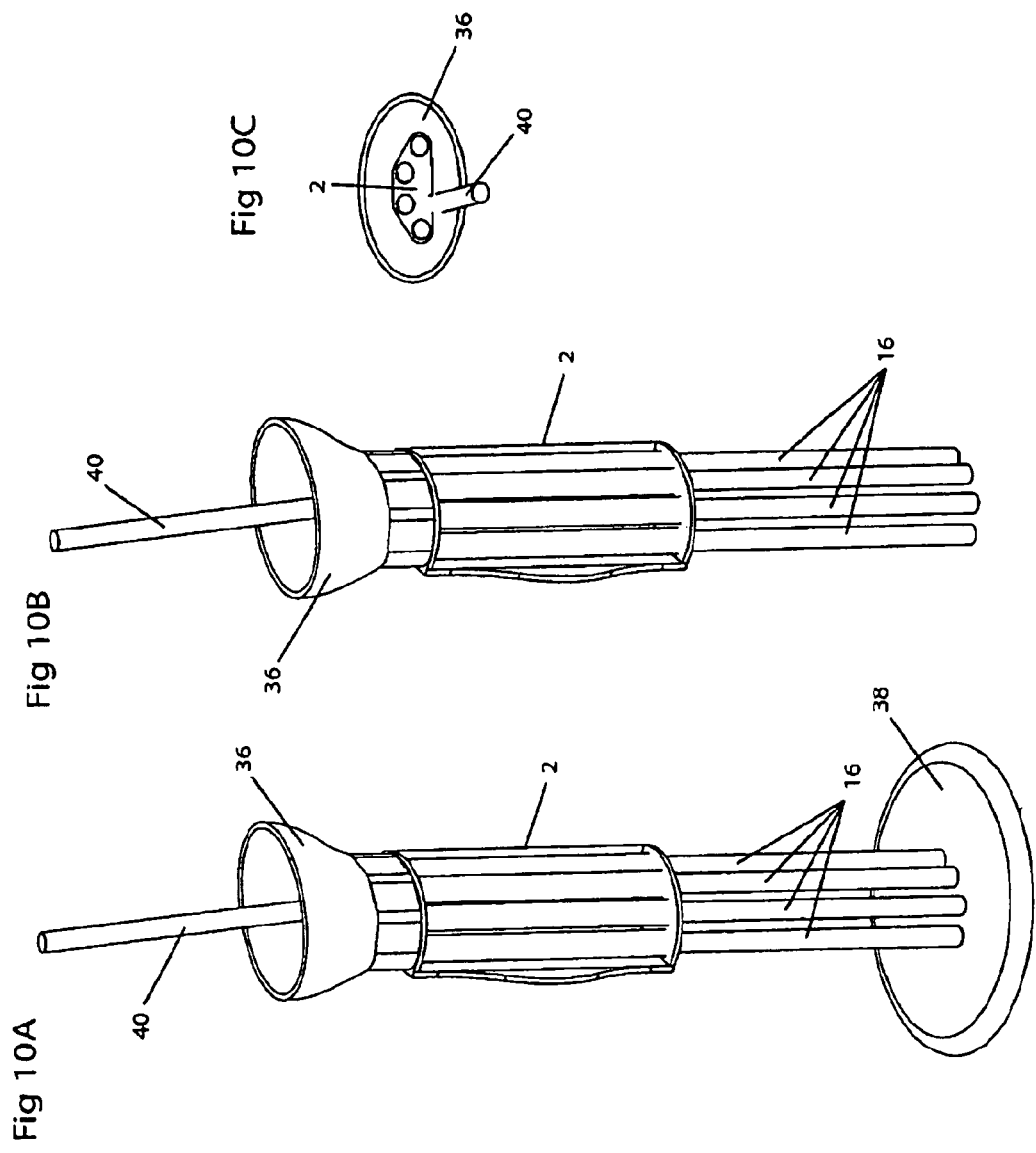

MEDICAL TREATMENT MATERIAL DELIVERY APPARATUS

BACKGROUND

The present invention is directed to the field of delivery apparatus for delivering bone cement material or the like to the human or animal body.

There are certain medical procedures in which it is desirable to inject orthopaedic material into a patient.

One such known procedure is to treat a spinal column with degenerative intervertebral discs by permanently stabilising adjacent vertebrae by fusion. The disc with a pathological disorder can lead to compression of adjacent nerve roots or the spinal cord causing chronic pain to the bearer. This painful affliction is suffered by a large number of people worldwide, particularly elderly people. Intervertebral fusion can relieve the pain. The aim of intervertebral fusion is to maintain the proper intervertebral spacing and eliminate relative movement between the vertebrae, thereby treating the cause of the pain.

The spinal fusion procedure involves the replacement of the damaged, dislocated or degenerative disc with an area of fused bone. In order to encourage such bone fusion, a bone growth stimulant is used. The placement of this bone growth stimulant between the vertebrae is often carried out by insertion of an implant between the vertebrae, where the implant contains the stimulant and offers a framework for carrying the stimulant. The implant with bone growth stimulant causes bone growth in and around the implant and across the intervertebral space, thereby fusing the adjacent vertebrae into one bone mass.

Known bone growth stimulants are often granular materials. For example, autograft bone (donor bone harvested from the patient's body) or allograft bone (bone from cadavers) chippings or fragments are used, usually together with implant material such as powder/liquid material such as calcium based sulphates and phosphates.

There are other procedures in which bone graft is used in surgery, such as some forms of revision surgery.

Appropriate location of the bone growth stimulant is essential to encourage new bone growth. This placement can be difficult as the application site is often in parts of the body which are difficult to access. The use of minimally invasive procedures is preferable as it reduces trauma to the patient. Such procedures require a delivery device which can be carefully controlled by the surgeon and also which have thin delivery nozzles or ports.

Conventionally, a granular bone growth stimulant is prepared in paste form and is delivered to an application site by means of a syringe or a funnel. For example, in the case of spinal fusion, pre-loading of cages with a paste of bone growth stimulant is performed, the cages are then implanted and further paste is loaded in and around the cages. This is currently done using a tapered funnel and a spatula. The use of a tapered funnel and spatula is messy and time-consuming and does not offer the clinician sufficient control of the bone growth stimulant delivery, which is all important for a successful operation. Further, the granular material can clog in the tapered section.

Other delivery devices are known for delivering orthopaedic material. In general, these include a cylinder in which the material is held (or, in some cases, mixed). The material is then forced out of an end of the cylinder by means of, e. g., a plunger or piston into a narrower or tapered delivery nozzle for delivery to the desired site. Although such systems are useful for fluid or less viscous materials, they have not proved suitable for delivering thick pastes or highly viscous materials or for delivering materials containing relatively large chips or granules such as the bone graft materials described above. In the latter case, the transition to a narrower or tapered outlet can result in the granules separating from the paste, thereby delivering a composition, which is, at best, diluted of the granular bone growth stimulant. It may also be that the flow of the paste for delivery is prevented entirely or to an unacceptably high degree.

The present invention aims to overcome the disadvantages of known delivery apparatus for delivering thicker and/or granular materials.

SUMMARY

There is provided a delivery apparatus for delivering material to a medical treatment site, comprising:
  a plurality of containers for said material;
  a dispensing outlet;
  means for bringing each container into communication with said outlet; and
  means for transferring the material from the containers and through said outlet; and wherein said containers have a uniform cross-sectional area along their length.

The plurality of containers may be mounted in a cartridge or may be directly mounted onto or in another type of delivery apparatus for example a gun-type device similar to that described below. Features of the outlet, the means for moving the containers into alignment with the outlet and the means for transferring the material out of the tubes are preferably as set out below.

An improved flow is achieved by the use of a delivery apparatus having a plurality of containers, as opposed to just one container. In this way, for an apparatus for containing a certain amount of material, several small bore tubes or the like can be used and can dispense material via a similarly sized outlet, rather than using a single large bore cylinder and then dispensing via a smaller outlet. Accordingly, tapering can be reduced or eliminated, thereby improving flow properties of the delivery apparatus. If a suitable number of containers are provided of suitable volume, the required amount of granular material can be delivered to the patient in a single operation, without re-loading.

The use of several narrower containers is advantageous as the amount of force needed to move the granular material through each individual container is reduced as compared to a single large container. According to the present invention, this narrowing is achieved without compromising the total volume of granular material deliverable by the use of the apparatus.

Whilst each individual container could have its own outlet, which may be the distal end of a respective dispensing nozzle, in a preferred form of the present invention, the outlet is formed at a distal end of a dispensing nozzle common to all of the containers. Preferably, the containers and the outlet nozzle have a uniform cross-sectional area along their length. Preferably, this uniform cross-sectional area of the containers and the outlet nozzle is the same. Preferably, the containers are cylindrical and the outlet nozzle is cylindrical along at least a major portion of its length.

In one form, a distal tip portion of the outlet nozzle includes a planar outer surface. Such a surface will provide improved mating with a flat vertebral disc portion. The distal tip portion could be rectangular or square in cross-section, for example. A cross-sectional width of the distal tip portion and the remainder of the outlet nozzle should remain substantially constant so as to avoid the material to be delivered becoming blocked. In one form, the outlet nozzle could comprise a distal tip portion with a planar outer surface, wherein the distal tip portion has a cylindrical bore with an inner diameter matching an inner diameter of the remainder of the outlet nozzle where the remainder is cylindrical.

Accordingly, a delivery system is provided without the need for a step-down or taper between the containers and the nozzle.

Thus in a preferred embodiment, each container, when aligned with the outlet, defines a passage having a substantially uniform cross-sectional width extending to the outlet. More preferably, the passage is cylindrical up to a distal tip portion and possibly along the entire length. Thus, no tapering is required before the granular material is to be dispensed.

The device is provided with some means, e. g. a plunger, for pushing the material out of the containers via the outlet. A single plunger may be used or, alternatively, each container may have an associated plunger.

According to a preferred embodiment, the containers are mounted within a cartridge. In one of its simplest arrangements, the cartridge could be operated by hand, whereby the user manually pushes the material out of each container—preferably one at a time—using the plunger(s).

The following preferred forms of the delivery apparatus, however, serve to ease the process of applying the material to an application site.

In one preferred form, the application process is eased by sequentially bringing each of the plurality of containers into communication or alignment with the outlet. Thus, the user, after use of one of the containers, can then move the plurality of containers so that the next one is aligned before material delivery can re-commence. This is convenient as compared to having to sequentially re-fill a container after it has delivered cement or replacing it with a full one after delivery.

The sequential movement may be carried out using a manual indexing method. In this form, the user can dispense the material from one of the containers and then re-position sequentially the next full container into alignment with the outlet by hand.

Preferably, however, the apparatus is, provided with means for automatically sequentially bringing the containers into line with the (common) outlet. In one form, the cartridge can move to sequentially the next position, i.e. so that a next container is brought into alignment with the outlet, as soon as the current container has had its material dispensed. In an alternative form to moving the cartridge as a whole during this indexing operation, the containers can move within the cartridge. Automatic indexing of the containers after dispensing is useful as it allows the user to concentrate more exclusively on the delivery of the material rather than working of the apparatus.

In one embodiment, the cartridge is biased, when a plurality of loaded containers are operative, to move a next container to an aligned position with the outlet. Accordingly, once a container is spent of the material, the biasing force will automatically move the cartridge to the next position.

In order to facilitate the operation of this automatic sequential indexing movement, the preferred delivery apparatus comprises a stop configured to prevent the biasing force moving the cartridge to align the next container. In one form, the stop is arranged against a plunger of an aligned container such that once the plunger is past the stop, the bias moves the cartridge to align the next container. In this way, the biasing force is only effective to index the cartridge to the next position once the plunger has been depressed. That is, once the material has been delivered.

In a preferred embodiment, the containers are tubular. Also preferably, the outlet is formed at the end of a nozzle outlet, which is itself a container, preferably tubular, the same as the containers of the containment portion of the delivery apparatus, hi this way, only one set of elements needs to be manufactured for both the outlet nozzle and the containers. These can then be mounted to the delivery apparatus and no tapering portion between the nozzle and the containers will be necessary.

In a further preferred form, the containers are removable from the cartridge. The cartridge thus provides a disposability aspect to the delivery apparatus such that the containers are one time use only. This may be advantageous for reasons of cleanliness and because of the difficulty in cleaning thin containers. The outlet nozzle may also preferably be removable from the cartridge to provide a further disposable element. Accordingly, these elements of the apparatus in contact with the material to be delivered are disposable.

Preferably, the delivery apparatus is provided with a cap mounted to the cartridge. Preferably, the cap includes a nose portion. More preferably, an outlet nozzle in the form of the containers is mounted to the nose portion and extends distally from it, forming a nozzle outlet for the delivery apparatus. Preferably, the cap is removable, the nozzle outlet is removable, the containers are removable and the cartridge is removable. This provides a disposability aspect as well as aiding a cleaning process.

There are currently two alternative preferred forms for the cartridge. The first is a generally cylindrical cartridge where the containers are mounted about the axis of the cylinder. Preferably, the apparatus comprises means for rotating the cartridge about a longitudinal axis. The second preferred form is a flat or planar cartridge, e.g. an oblong shaped cartridge.

The containers of the cartridge should preferably be provided with an end for loading the material into each cartridge from outside of the cartridge to ease the pre-loading process. In a related preferred aspect, the cartridge is preferably adapted to receive a clip-on funnel at one end to allow easy loading of the containers with the material. Preferably, the containers are tubular members mountable to the cartridge body in a manner such that they terminate at both longitudinal ends of the cartridge.

For the purposes of delivering the material, each container preferably includes an end for receiving a plunger from outside of the cartridge and an opposite end for delivering the material from the tubular container to the outlet.

The preferred delivery apparatus further comprises a drive unit in the form of a gun onto or into which the cartridge unit is mounted.

As discussed above, ejection of the material from the containers is achieved by the delivery apparatus preferably comprising a means for effecting the delivery of said material, such as a plunger. A plunger provides control over the amount of material being delivered. In another form, the delivery apparatus can comprise a plurality of plungers respectively mounted to each container.

The plunger(s) may be manually operated, but delivery is easier to perform if the apparatus comprises an advancement means for advancing the plunger(s) through one or a respective one of said containers. The advancement means may comprise a gripping means for gripping a plunger to move it along its path. For handling convenience, the advancement means may comprise a trigger arranged to transfer its movement force to the gripping means.

In a preferred form, both the outlet and the containers are sized to be capable of sealingly accommodating the same plunger. In this way, all of the material in the containers and in the outlet can be removed with one (or one set of) plunger(s).

In other preferred forms, the containers have a cross-sectional width (or diameter in the case of cylindrical containers) for containment of up to 8 mm, preferably up to 7 mm, preferably up to 6 mm and preferably a diameter of about 5 mm. As described above, the forces needed to deliver the material from the containers are reduced as the cross-section of the containers approaches that of the outlet. Accordingly greater control over the delivery location is possible. The small diameter containers require corresponding small recesses, thereby allowing minimally invasive surgery techniques. 5 mm single tubes are available and are considered an appropriate size for the containers with regard to balancing sufficient containment volume with minimising the opening to the human body required. The use of narrow containers in the present invention is compensated, in terms of deliverable volume of material, by the provision of a plurality of such containers in a single delivery apparatus or cartridge.

In a preferred form, in order to allow anterior access to a spinal column, the outlet is in the form of a nozzle which is preferably at least 120 mm in length. It is advantageous to use thin outlet nozzles so as to allow minimally invasive surgical procedures to be used. In one preferred from, an outside cross-sectional width (or diameter in the case of a cylindrical outlet nozzle) of the nozzle is a maximum of 8 mm. An outlet nozzle with a minimal cross-section being provided with granular material from a container without a taper in-between necessarily requires the container to also be of minimal cross-section. A container with a minimal cross-section will have a reduced material containment volume for a given length of a larger cross-sectioned container. This reduced containment volume is compensated by the provision of a plurality of containers.

Exemplary embodiments will now be described, by way of example only, with reference to the figures.

BRIEF DESCRIPTION OF THE DRAWINGS

FIG. 10 shows part of the first embodiment.

DETAILED DESCRIPTION OF THE INVENTION

Figure 1:
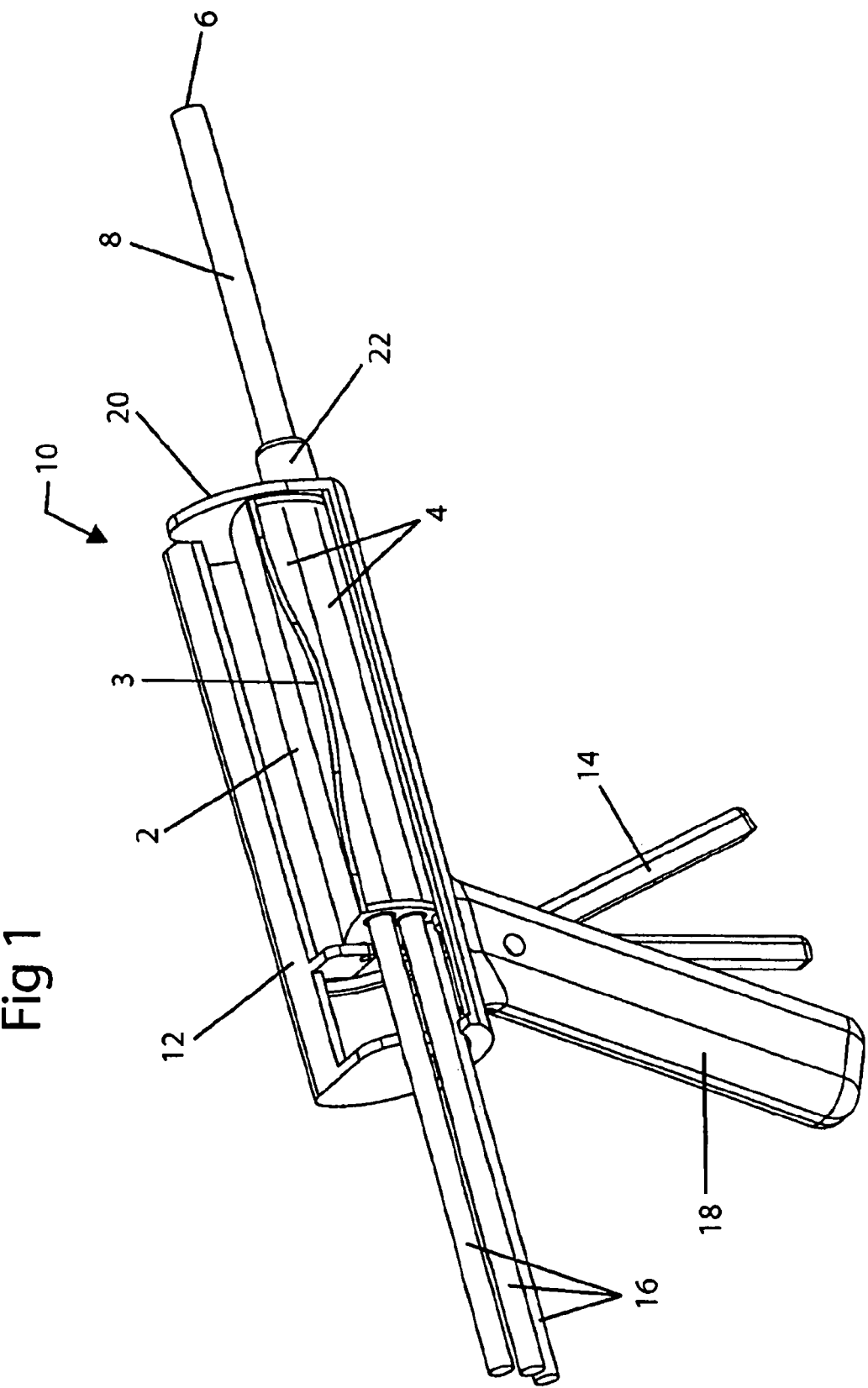
FIG. 1 is a part-sectional view of a first embodiment.

A means is provided for delivering a material, preferably a granular material, such as a paste comprising bone fragments or other granular bone growth stimulant, to a joint between bones to be fused, particularly between vertebrae. The delivery means comprises a plurality of containers for containing the material to be delivered and also comprises an outlet from which the material is to be delivered.

The plurality of containers are mounted to the delivery apparatus such that they are sequentially moveable into an aligned position with the outlet. In preferred forms, the delivery means comprises a cartridge comprising the plurality of containers, and the cartridge itself is mounted in the sequentially moveable manner. Alternatively, the containers themselves may be moveable either in relation to a fixed cartridge body or in relation to a fixed delivery gun or the like on or in which the containers are mounted.

The cartridge may be removed from the remainder of the apparatus and a funnel attached to it. Bone growth material is placed into the funnel and, in turn, forced into the respective containers of the cartridge. The containers are thus loaded.

The delivery apparatus may comprise plungers mounted to one end of each of the containers. These plungers may be manually operated, but the delivery apparatus may also comprise an advancement mechanism comprising a trigger mechanically linked to a gripper. The gripper is adapted to grip the rod and move it through the container, which is presently aligned with the outlet, upon actuation of the trigger. This effects the required granular bone growth material delivery.

The cartridge of the delivery apparatus may be biased in favour of moving the next container to the aligned position. This is resisted by a stop, which rests against the plunger until it is fully depressed. Once fully depressed, the stop is no longer effective to maintain that container in the aligned position and the bias will operate to align sequentially the next container.

The outlet of the delivery apparatus is preferably provided at the end of a container of the same form and dimensions of the containers of the cartridge, but mounted to the delivery apparatus so as to extend distally away from the cartridge and provide an outlet nozzle. This "delivery container" should be mounted to a nose portion of the delivery apparatus. The aligned container will deliver bone growth material into the outlet nozzle in the nose portion.

Once all the containers of the apparatus have been spent in delivery, each will be filled with its plunger, but the outlet nozzle will still be full of bone growth material from the last container of the cartridge. This can be dealt with by feeding a further plunger through the last container to force the plunger in the last container of the cartridge into the outlet nozzle, thereby expelling the bone growth stimulator material contained in it. The last tube of the cartridge could be pre-loaded with a plunger rather than bone growth material to facilitate this flushing operation.

After use of the delivery apparatus, the outlet nozzle and the containers may be removed and disposed of. The remainder of the apparatus may be re-used with replacement containers. Alternatively, the cartridge itself may be disposable, meaning that a replacement cartridge would be used.

FIG. 1 shows a side view of a first embodiment of the delivery apparatus. In the first embodiment, the delivery apparatus 10 includes a cartridge 2 having mounted therein a plurality of tubular containers 4. While the containers 4 are shown in tubular form, other cross-sectional shapes are possible.

The delivery apparatus includes an outlet 6 at a distal end of a tubular outlet nozzle 8. The tubular outlet nozzle 8 is in communication with one of the plurality of tubular containers 4 so that a granular paste of bone growth stimulant can pass between them. The outlet nozzle 8 is shown as tubular, but other shapes are possible. In particular, an outlet nozzle 8 with a distal tip portion which includes a planar outer surface may be preferable for improved insertion into a planar portion of an intervertebral space. The cross-sectional width of the outlet nozzle 8 should remain constant to the outlet 6 and in one form, the inner cross-sectional shape of the outlet nozzle 8 is the same up to the outlet 6. The distal tip portion with the planar outer surface could be provided as an attachment.

The outlet nozzle 8 could be a tubular container as used in the cartridge 2. It may be that the outlet nozzle is mounted to a nose portion 22 of a cap 20. The cap 20 with the integral nose portion 22 is mounted over the distal end of the cartridge 2 in a rotatable manner to allow the indexing function described below.

The delivery apparatus 10 includes a housing 12 to which the cartridge 2 is mounted. The cartridge is mounted in such a way that movement, in this embodiment rotation, of the cartridge 2 relative to the housing 12 is possible. For example, the cartridge 2 could include a projecting spindle 42 (FIG. 7) and the housing a complementary recess (not shown). The cap 20, which is mounted over the cartridge 2, will be mounted fixedly to the housing at a distal end and the spindle 42 mounted to a corresponding recess at a proximal end. The cartridge is thus able to rotate relative to the housing 12 and the cap 20. The rotatability of the cartridge 2 permits the containers 4 to be sequentially alignable with the outlet nozzle 8. A container 2 aligned with the outlet nozzle 8 is said to be in the aligned position.

The delivery apparatus 10 includes a plurality of plungers 16, respectively mounted to the proximal end of each of the plurality of containers 4. The plungers 16 extend proximally from the cartridge 2 and further extend proximally from the housing 12. The plunger extending from the container which is in the aligned position is addressed by a gripper 34 (FIG. 2) of the delivery apparatus 10. The gripper is mechanically linked to a trigger 14 such that translational movement of the trigger 14 causes translational movement of the gripper 34 causing a translation of the plunger within the container in the aligned position. The delivery apparatus 10 is provided with a handle 18. The trigger 14 is pivoted about an upper portion of the handle 18 and is biased away from the handle 18.

Advancement of the plunger through the container (in the aligned position) forces the granular paste towards the outlet 6 through the passage between the outlet nozzle 8 and the container. Thus, squeezing and releasing the trigger causes a pumping of the paste towards and out of the outlet 6. The bias of the trigger 14 away from the handle 18 provides a restoring force to the pumping cycle.

The delivery apparatus 10 of FIG. 1 includes an automatic alignment or automatic indexing feature. The cartridge 2 of FIG. 1 is biased such that after the plunger of the container in the aligned position is pumped beyond the gripper 34, the cartridge 2 automatically rotates to align sequentially the next container with the outlet nozzle 8. The gripper 24 acts as a stop to prevent further rotation of the cartridge 2 while the associated plunger still extends beyond the gripper 34.

The bias force of the cartridge of FIG. 1 is provided by use of gravity. The cartridge 2 is shaped such that the bias will continue to exist until the last paste-filled container is in the aligned position. In particular, the cartridge may include a bulbous portion adjacent the last filled container to ensure sufficient gravitational effect.

The cartridge 2 includes a tab 3 to allow easy manoeuvring of the cartridge 2 by the operator.

Figure 2:
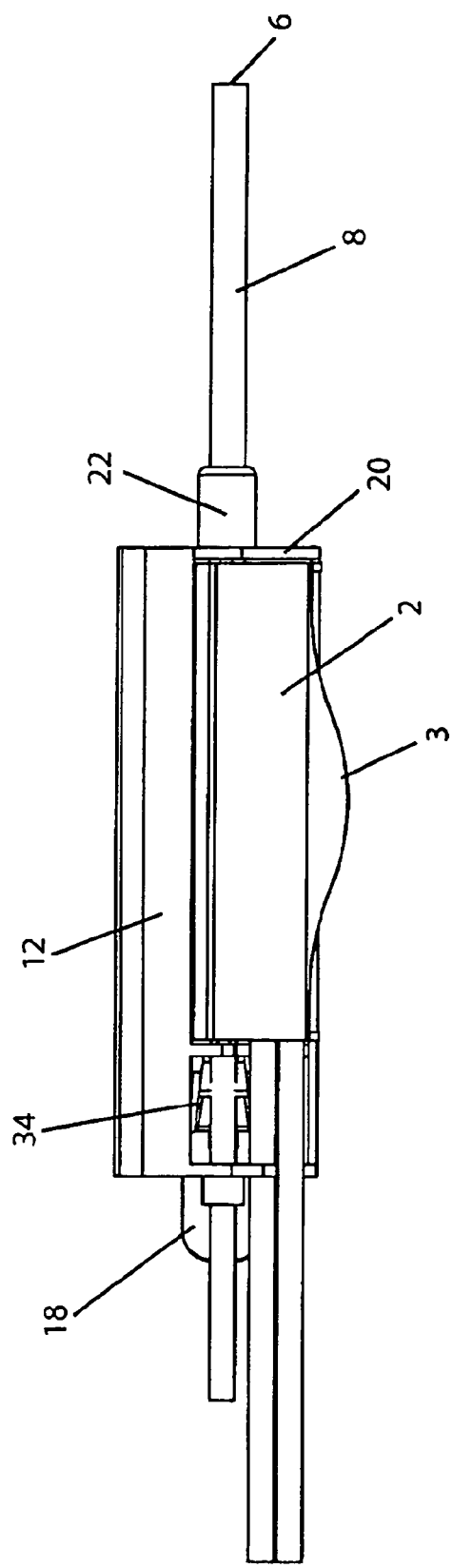
FIG. 2 is a further part-sectional view of the first embodiment.
Figure 3:
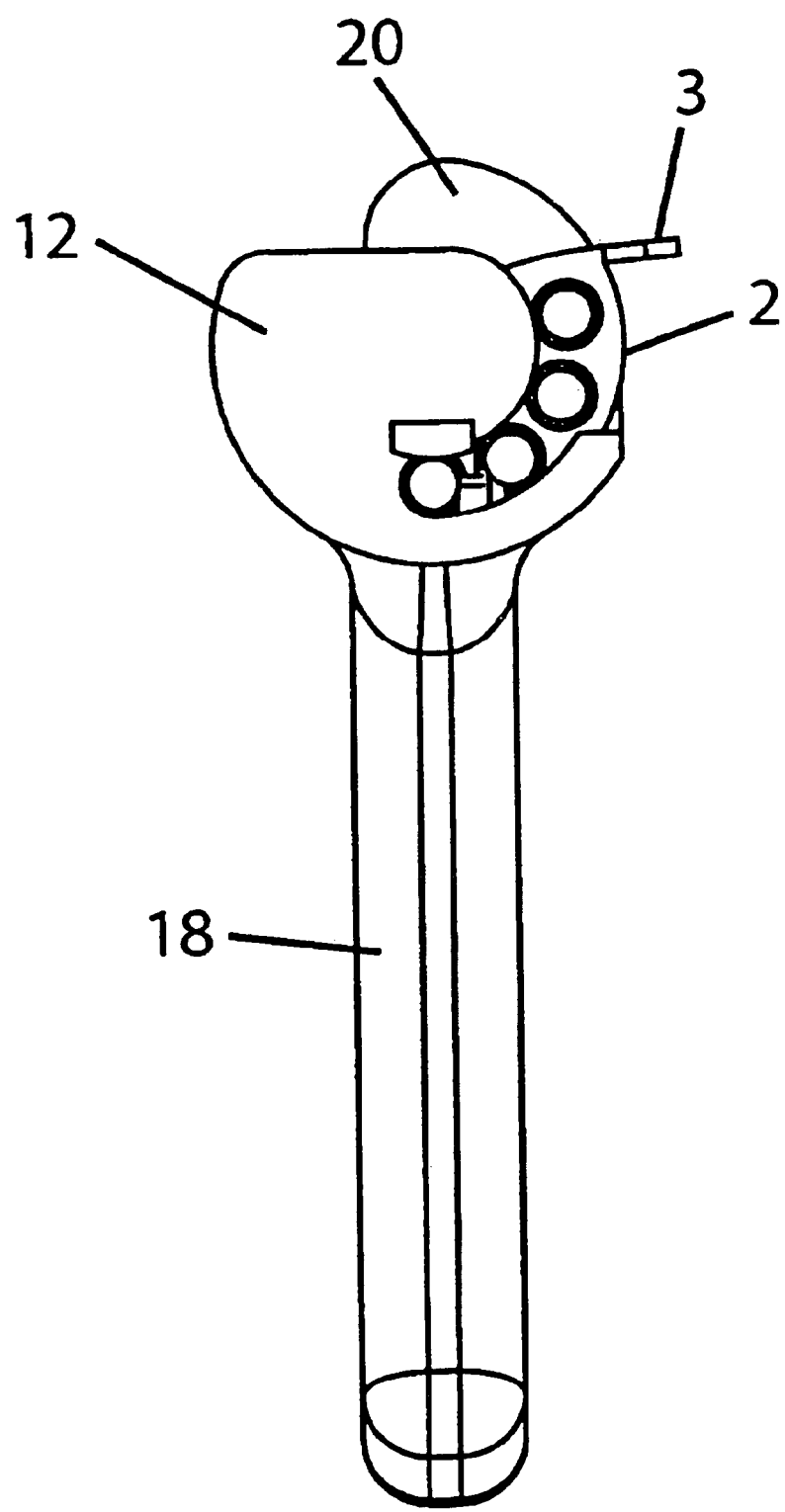
FIG. 3 is an end, part-sectional view of the first embodiment.

FIG. 2 discloses a rear end view of the delivery apparatus 10 of FIG. 1 and FIG. 3 shows a view from above. The view from above shows more clearly the gripper portion 34 described above. It can be seen from FIG. 3 that it is not until the plunger moves beyond the gripper that the cartridge 2 will be able to index into the next position.

The delivery apparatus 10 of the first embodiment is in the form of a revolver gun, whereas the delivery apparatus of the second embodiment is in the form of an automatic rifle, with a flat cartridge 102. A perspective view of a second embodiment with a flat cartridge is shown in FIG. 4.

The housing 112 of the second embodiment is shaped so as to accommodate a planar cartridge 102. The housing of the first embodiment allowed the plungers 16 to extend proximally beyond the housing 12 by means of an opening in the proximal end of the housing 12. The housing 112 of the second embodiment, on the other hand, houses the full length of the cartridge 102 and the proximally extending plungers 16.

The flat cartridge 112 is laterally moveable relative to the housing 112. The delivery apparatus 10 includes a biasing means to bias the cartridge to moving to align the next filled container with the outlet passage 8. The housing 112 is provided with a gap in its side walls on either side of and the length of the cartridge 102. The gap allows the cartridge to freely move laterally beyond the housing without obstruction, thereby permitting indexing to the last container of the cartridge 102. The gap extends the length of the cartridge 102, but not the full length of the plungers 16 extending proximally from the cartridge 102. Thus, it is not until that the plungers 16 are depressed within the containers 4 of the cartridge 102 that the cartridge 102 is capable of laterally indexing, through the gap, laterally beyond the sidewalls of the housing 112.

Figure 4:
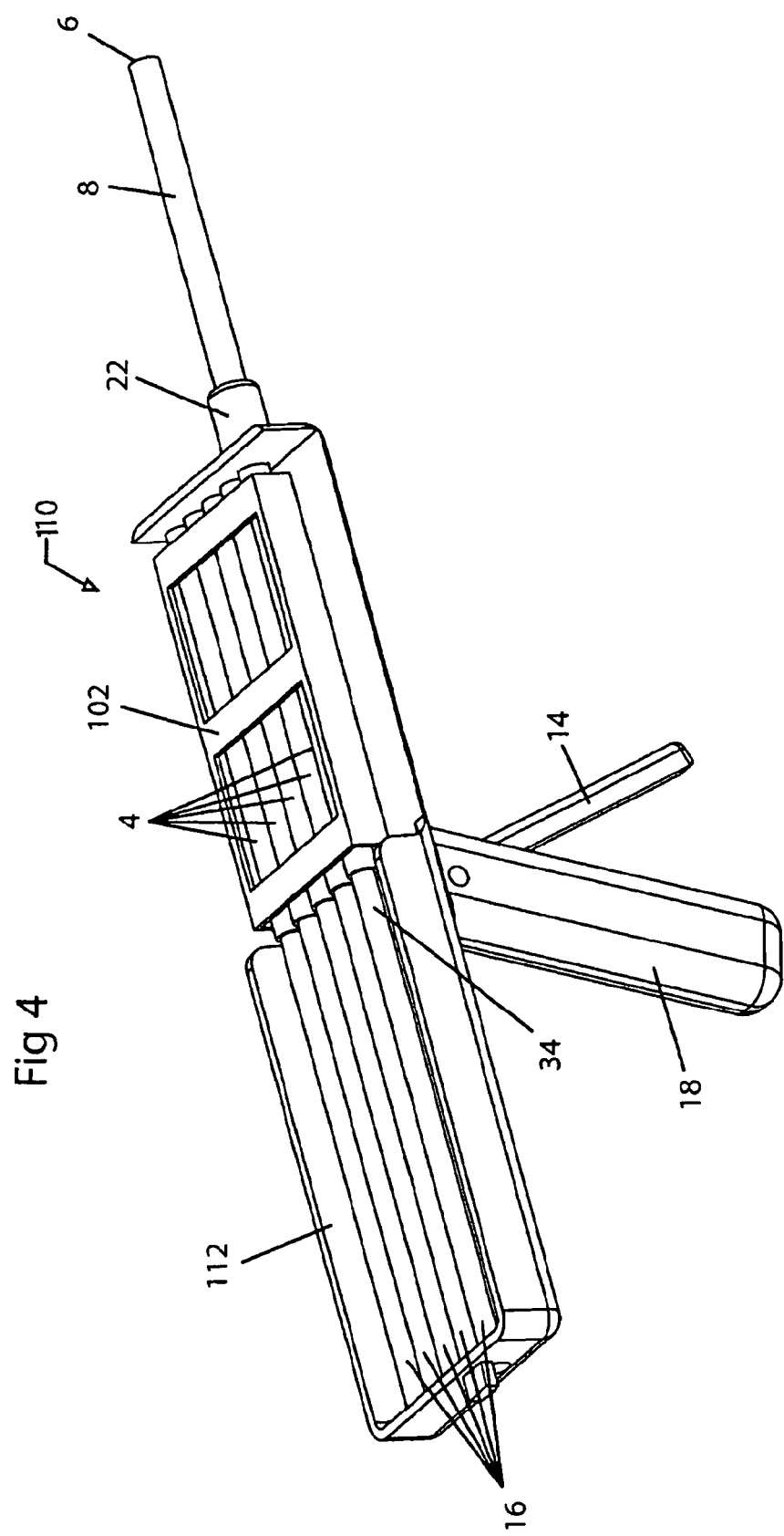
FIG. 4 is a perspective view of a second embodiment.
Figure 5:
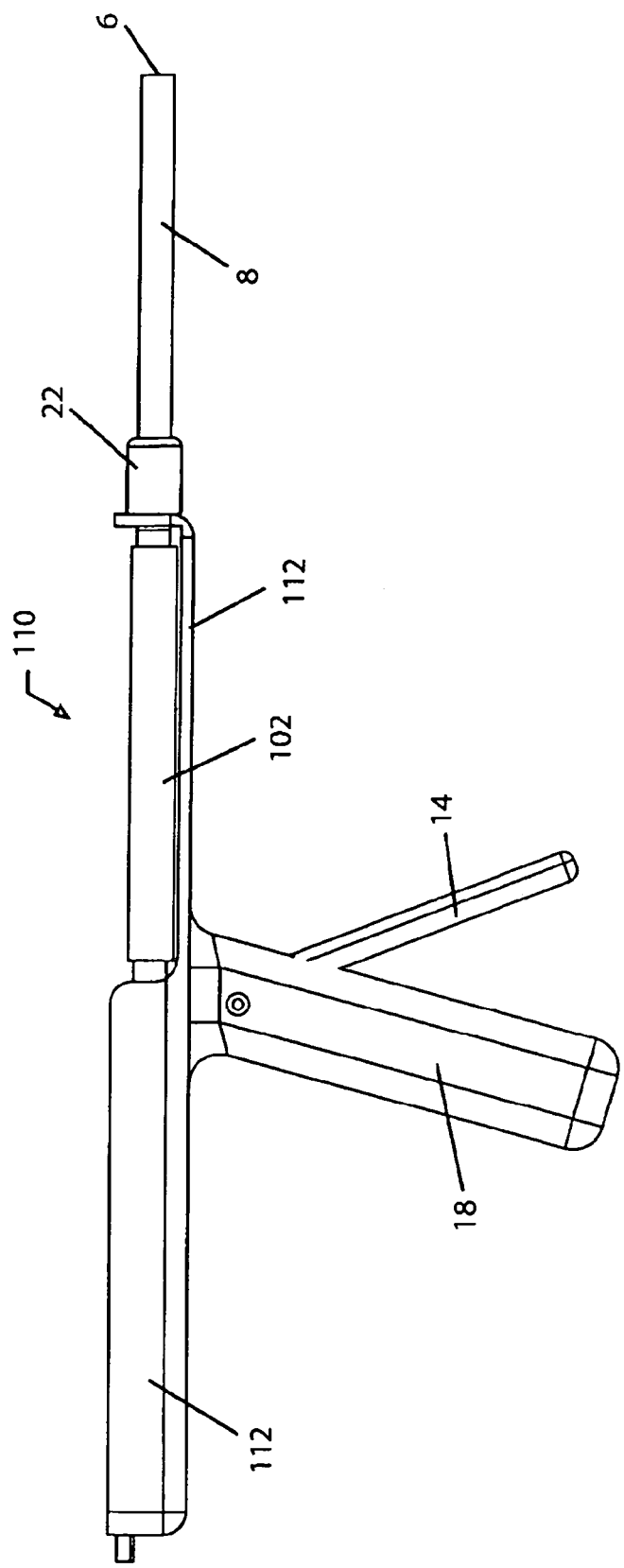
FIG. 5 is a side view of the second embodiment.

Further illustration of the delivery apparatus 110 of the second embodiment is shown in FIG. 5, which is a side view of the delivery apparatus 110 of FIG. 4.

The remaining features of the second embodiment are similar to corresponding features of the first embodiment and so require no further discussion.

The delivery apparatus 10, 110 may be provided as a kit of parts which may be assembled to form the delivery apparatus and disassembled after use. This means that elements of the apparatus can be disposable, particularly elements in contact with the paste of bone growth material as they can be difficult if not impossible to clean.

Figure 6:
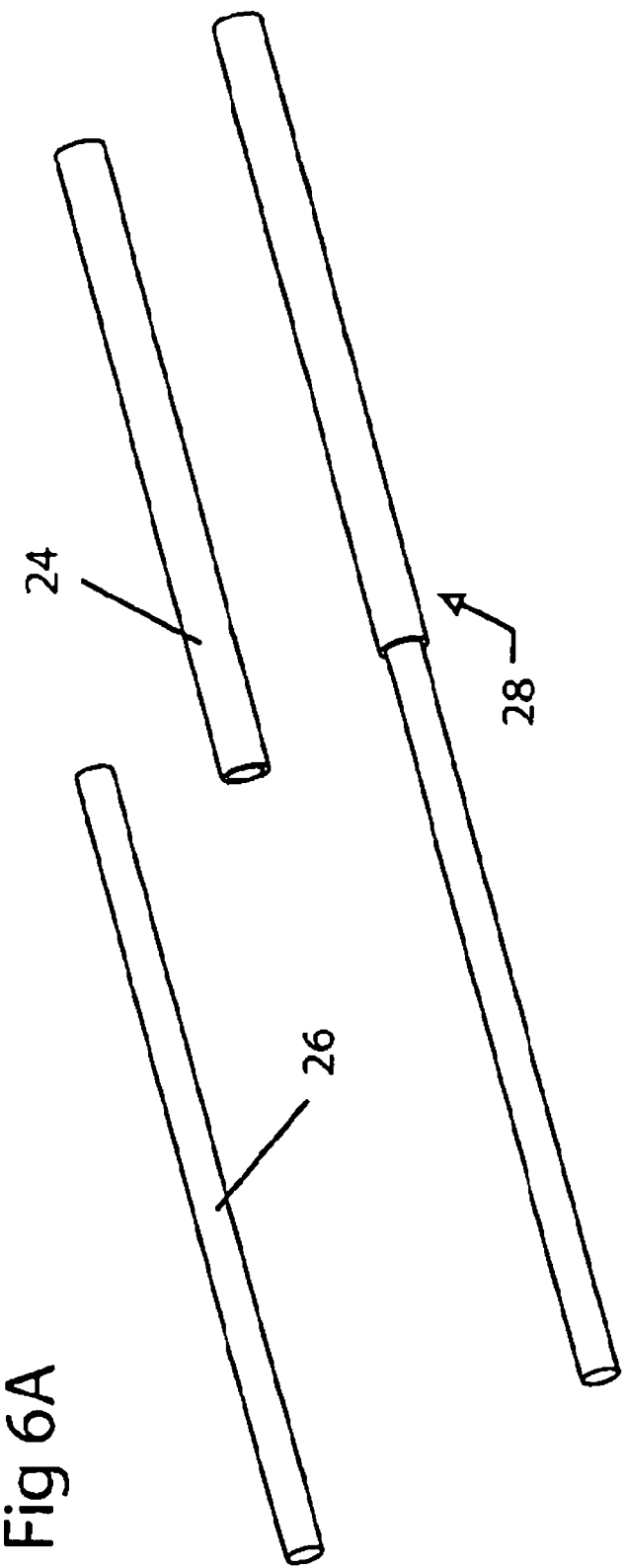
FIG. 6 shows an example of part of a preferred embodiment.
Figure 7:
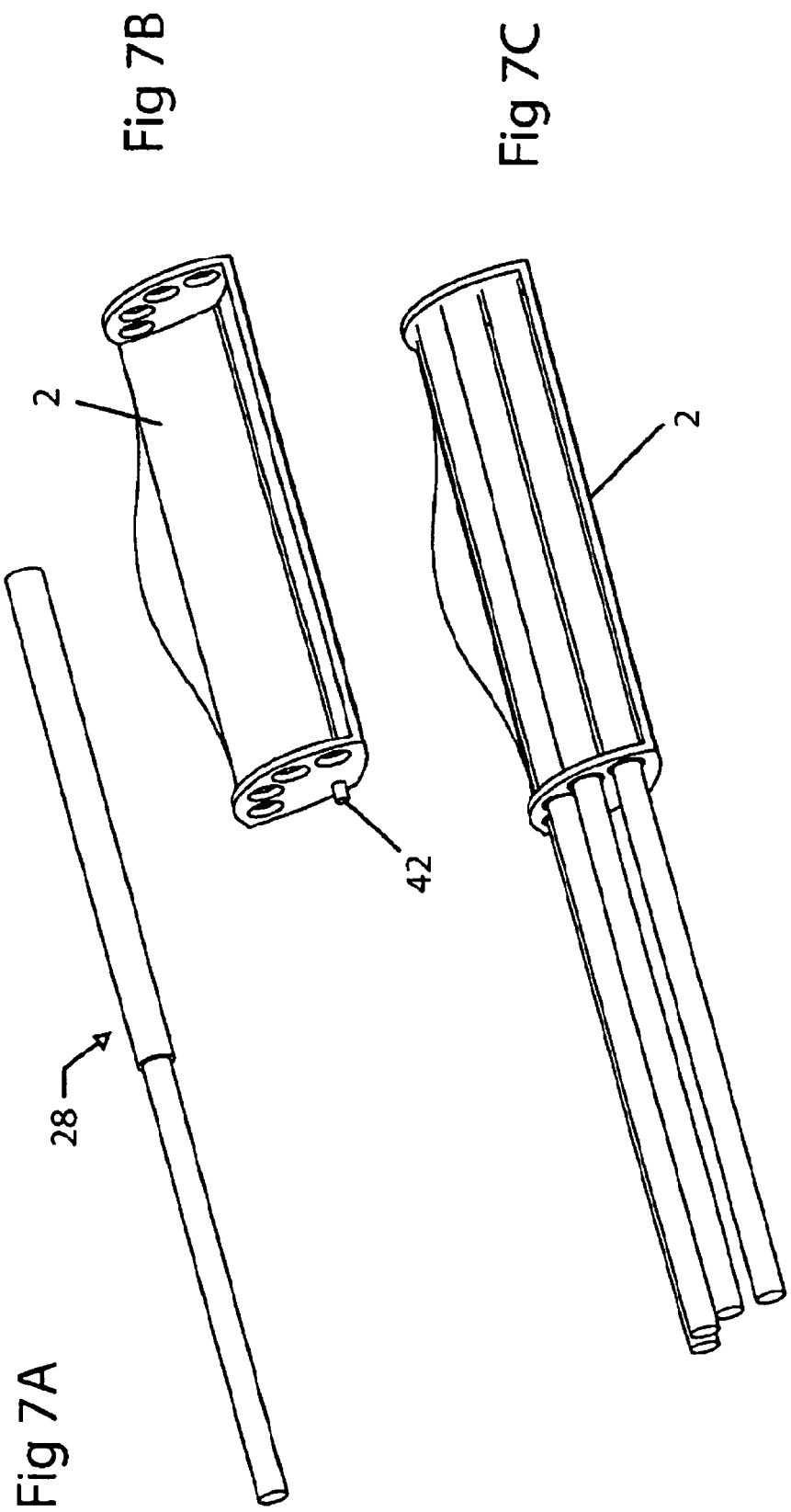
FIG. 7 shows part of the first embodiment.
Figure 8:
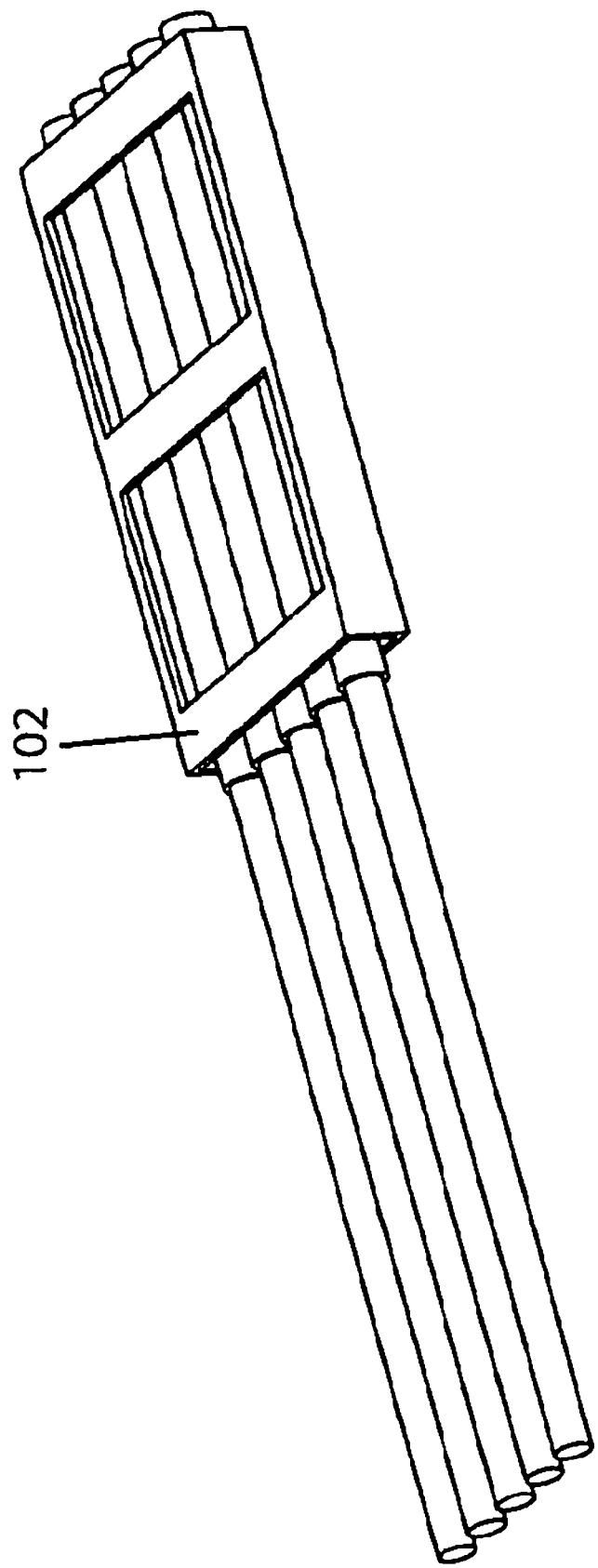
FIG. 8 shows part of the second embodiment.

The tubular containers 4 are preferably disposable elements of the delivery apparatus 10, 110. FIG. 6 shows an individual tubular container 24. The plunger 26 is in the form of a push rod and can be mounted to a proximal longitudinal end of the tubular container 24 to form the assembled push rod and cement tube shown in FIG. 6. The required number of containers can be assembled in this way and mounted to the cartridge 2 or 102 as shown in FIG. 7 or FIG. 8 to provide a cartridge suitable for use with a delivery apparatus 10, 110. The push rods 16 could be mounted to the containers 14 after the containers have been mounted to the cartridge 2.

Figure 9:
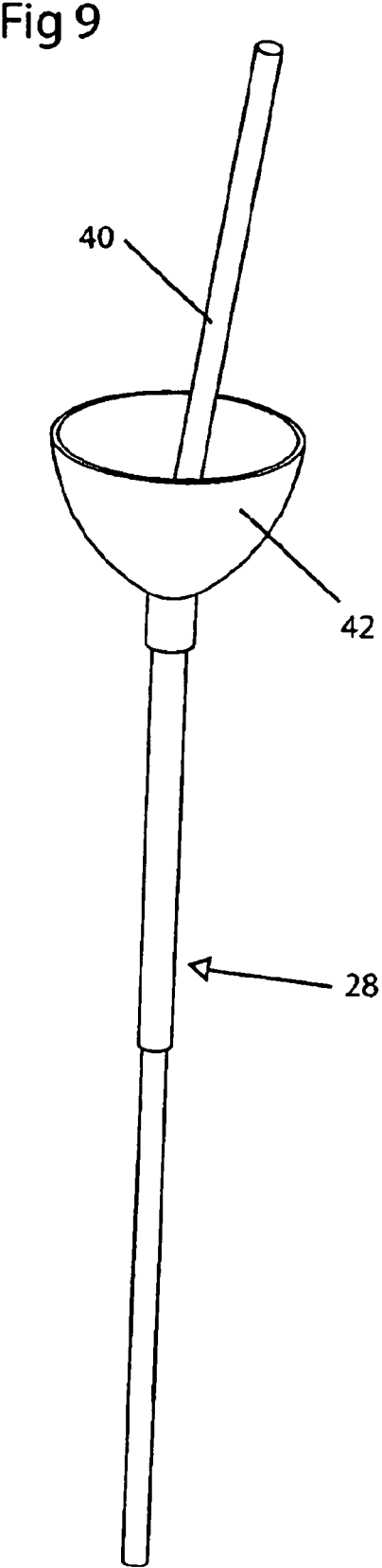
FIG. 9 shows part of a preferred embodiment.

The containers 4 may be pre-loaded with the granular bone growth material before mounting to the cartridge as is illustrated in FIG. 9. FIG. 9 shows a funnel 42 with a spout fittable to a single container 24, which is shown in the figure as being pre-mounted with a push rod 26. The spout should be clipped to the container 24 so that cement in the funnel 42 can be delivered through the spout and packed into the container 24 with a rod 40. This pre-loading of the containers 4 is particularly suitable for the second embodiment where the cartridge 102 is flat.

Figure 11C:
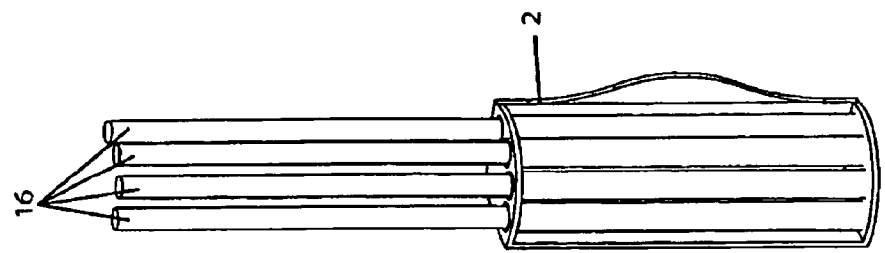
FIG. 11 further shows part of the first embodiment.
Figure 11B:
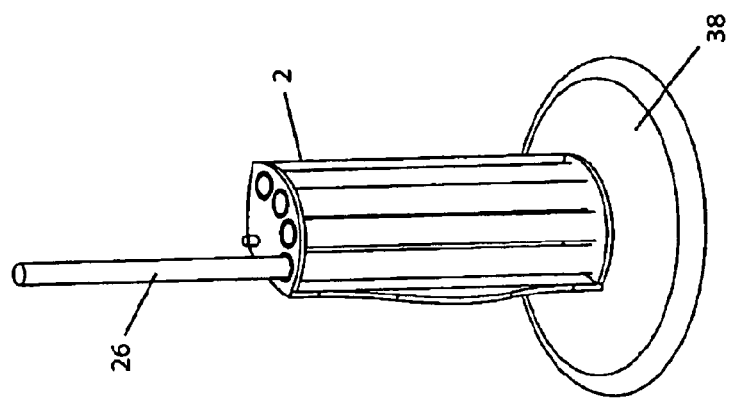
Figure 11A:
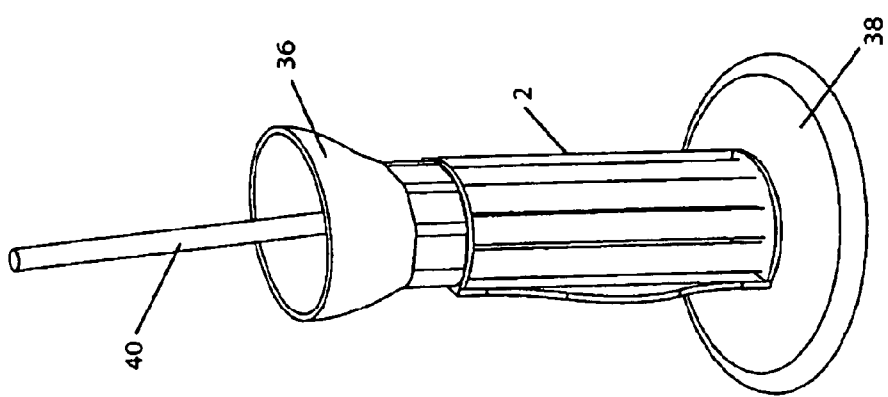

Alternatively, a clip on funnel 36 can be provided, which is mountable to an end face of the cartridge 2, as shown in FIG. 10. The end face may present a solid face to the spout of the funnel 36 with openings providing a passage to the tubular containers of the cartridge. The cartridge can be held by hand while granular bone growth material in the funnel is packed into the containers 4 using a rod 40. In FIG. 10, the push rods 16 are already mounted at the time of loading the containers 4. A more stable configuration is shown in FIG. 11, where the push rods 16 are mounted to the containers 4 after the loading is performed. A stand 38 may be provided to aid the loading process as shown in FIGS. 10 and 11.

The embodiments shown in the figures utilize a separate plunger for each container of the cartridge. It is, however, envisaged that a single plunger could be used. The drive of the delivery apparatus could drive the single plunger to expel the contents of a container in the alignment position. The plunger could then be retracted and the cartridge rotated so that the next tube is in the alignment position. The single plunger could then be pushed the length of the container in the next position. It is further envisaged that the cartridge could be manually indexed, rather than automatic. By manual indexing, it is meant that the user indexes the cartridge between aligned positions by hand. This is opposed to automatic indexing in that the cartridge is biased towards the next position by gravitational force or biasing force of a biasing means.

A method of use of the delivery apparatus of the first embodiment will now be described.

The user will be supplied with a cap 20 with integral nozzle 22, a multiple of container tubes 16, an outlet tube 8 and a housing 12 with handle 18, trigger 14 and gripper 34 attached to it, e.g. as shown in FIG. 1. These components form the delivery apparatus of a preferred embodiment.

A paste of granular bone growth stimulator will be mixed. This paste may include bone graft as the stimulator. Each tube 16 will be filled with the paste as will the outlet tube 8. As described above, this can be performed one tube at a time or can more quickly be performed by assembling the containers to the cartridge and using a funnel to pack each container with cement in one step. The outlet tube 8 will normally need to be filled separately.

The delivery apparatus 10 will need to be assembled. The containers 16 may be pre-filled during this process or not. Each of the containers 16 is mounted within the cartridge 2. The end cap 20 is mounted over a distal end of the cartridge. The outlet tube 8 defines the aligned container. The cartridge 2 and mounted cap 20 with outlet tube 8 attached is then mounted to the housing 12 of the delivery apparatus 10.

The cartridge 2 will be mounted to the housing 12 such that the cap 20 is fixed relative to the housing 12, but the cartridge 2 is rotatable relative to the housing 12 and rotatable within the cap 20. The cartridge is mounted so that the gripper 34 is positioned against the plunger of the container in the aligned position. The delivery apparatus is then ready to use.

The surgeon will appropriately position the outlet 6 at the desired application site. Pumping of the trigger to expel the bone growth stimulator in the pre-filled outlet tube 8 will be performed. This pumping action operates the gripper 34 to force the plunger of the aligned container to travel the full length of the container. Once the container moves beyond gripper 34, the cartridge automatically moves the next rod to the alignment position. The pumping action is continued for as long as bone growth stimulator is to be delivered. The cartridge 2 should be loaded with enough containers 4 to provide the desired amount of bone growth stimulator.

Once all the pre-filled containers have been emptied, the nozzle will still contain an amount of bone growth stimulator equal to the volume of the outlet tube 8 if it is smaller than the last of the containers 4 or otherwise equal to the volume of one of the containers 4. In order to expel this material, one further container of the cartridge 2 can have a plunger pre-contained in it. A further plunger is then fed partly or fully through the container with a plunger pre-contained in it. This will then force the pre-contained plunger into the outlet tube 8 expelling the material contained in it.

Alternatively, two plungers could be fed through at the end of the procedure or one extra long plunger.

After the operation, the tubular containers 4 have their plungers 16 now contained in them as does the outlet tube 8.

The delivery apparatus 10 can be disassembled and the used containers 4 and the outlet tube 8 with plungers contained in them can be disposed of.

The use of a plurality of containers with a delivery apparatus permits the containers to be sized to a width sufficiently small to reduce any taper between the outlet and container to allow the granular material to pass at a desired flow rate. In fact, taper can be eliminated entirely to optimize the flow, which is particularly realized with a path through the container and then to the outlet which has a uniform cross-section. The containers may be made very thin and the loss of volume compensated by the provision of a multiple of containers in one apparatus. Thus, the provision of more than one container provides flexibility in the size of the containers practically possible.

For example, it is envisaged that between 20 ml and 40 ml of bone growth stimulant may be required for a spinal fusion operation. According to the prior art, this would be applied with a funnel or syringe, which would both require a relatively large containment portion to deliver this amount of material or several application steps would be needed. However, a delivery apparatus is provided where the outlet can be appropriately sized to allow minimally invasive surgery and the container sized to match. This solves the flowability problem. In order to overcome the fact that the volume of bone growth stimulant contained has been reduced, a plurality of containers can be mounted. The number of these tubes can be altered as required in order to fulfill apparatus length constraints and desired size of the output nozzle as well as total volume of material to be delivered. Thus, the design of the containers can be performed with greater flexibility.

One example size of the containment tubes is 4 ml volume tubes having an outside diameter of 8 mm and a length of 120 mm. A length of 120 mm is considered suitable for reaching deep fusion sites, such as in anterior approach spinal fusion. A corresponding tube can be provided for the outlet nozzle. Thus, 5 tubes can be loaded to enable delivery of 20 ml of bone growth material. An 8 mm delivery nozzle permits a minimally invasive approach to surgery to be used.

The use of thin tubes as described above also has the advantage that smaller forces will be needed to extrude the bone growth material, thereby allowing a more stable and controlled delivery.

A plurality of containers provided in a delivery apparatus also allows a more continuous delivery of granular bone growth material as it does not require intermediate container replacement or container loading steps.

The provision of a cartridge to hold the containers allows a one-step fixing of a plurality of containers to a delivery apparatus. Further, a cartridge that can be mounted and removed from a delivery apparatus offers a simplified filling operation. The cartridge may be provided with a portion for the clipping of a funnel and may otherwise be adapted to allow a one-step loading of all the containers.

The removability of an outlet nozzle from the dispending apparatus and the removability of the containers means that portions of the apparatus in contact with the bone growth stimulator can be disposed of. This advantage is further realised by the provision of respective rods for each container, which allows the plunger used in the delivery process also to be disposed of with the containers. This disposability is especially useful in combination with aspects of the invention allowing thin containers to be used as cleaning can then be a problem.

The ability to index into the aligned position is also an important feature as it allows a more continuous delivery of the bone growth stimulator. This is important where thin tubes are being used with small volumes of bone growth stimulator. An apparatus with small delivery volume would need continuous refilling if it weren't for the use of a plurality of such containers in the apparatus. Indexing capability further facilitates the transition from the delivery from one container and the delivery from the next. An automatic indexing capability allows this transition to be performed without the surgeon having to take any extra steps during the application process.

Although the invention has been described in relation to spinal fusion procedures, embodiments of the invention would be useful in a wide range of procedures for delivering material to a treatment site.

The invention claimed is:

1. A delivery apparatus for delivering orthopaedic material to a medical treatment site, comprising:
    a housing;
    a cartridge mounted to said housing;
    a plurality of separate containers for containing said orthopaedic material removably mounted in said cartridge, said containers being removable from said cartridge to provide for containers with a fresh supply of orthopaedic material;
    a dispensing outlet;
    means for bringing each container into communication with said outlet; and
    means for transferring the orthopaedic material from the containers and through said outlet; and wherein said containers have a constant cross-sectional area along their length; wherein said outlet is provided at an end portion of a dispensing nozzle, said dispensing nozzle arranged to be axially aligned with at least one of said containers, and wherein said dispensing nozzle has a constant cross-sectional area along its length the same as the cross-sectional area of the plurality of containers with which it is aligned.

2. The delivery apparatus of claim 1, wherein said means for bringing each container into communication with said outlet is biased to move a next container into communication with said outlet once a container in communication with said outlet is spent of said material.

3. The delivery apparatus of claim 2, said means for transferring comprising a plunger mounted in each of said containers and said delivery apparatus comprising a stop member arranged to be positioned against a plunger of said container in communication with said outlet in order to maintain said container in communication with said outlet.

4. The delivery apparatus of claim 3, wherein said stop member is arranged such that once said container is substantially spent of said material, the stop member is no longer positioned against said plunger of said container in communication with said outlet and the means for bringing each container into communication with said outlet is allowed to bring said next container into communication with said outlet.

5. The delivery apparatus of claim 1, wherein said means for bringing each container into communication with said cartridge comprises said cartridge being rotatably mounted to said housing such that said cartridge is biased to rotate until a last container is in communication with said outlet.

6. The delivery apparatus of claim 1, wherein said outlet is provided at an end portion of a dispensing nozzle mounted to said housing.

7. The delivery apparatus of claim 1, wherein said end portion comprises a planar outer surface.

8. The delivery apparatus of claim 1, wherein said housing and said cartridge are arranged so that the dispensing nozzle can be removed and replaced with others.

9. The delivery apparatus of claim 1, wherein said containers are tubular.

10. The delivery apparatus of claim 1, wherein said means for transferring comprises a plunger mounted within said containers, the delivery apparatus comprising an advancement means for advancing a plunger through a container in communication with said outlet.

11. The delivery apparatus of claim 10, wherein the advancement means comprises a gripping means for gripping the plunger and moving it along its path.

12. The delivery apparatus of claim 10, wherein said advancement means comprise a trigger for manual operation, said trigger arranged to transfer its movement force to the gripping means.

13. The delivery apparatus of claim 10, wherein both the outlet and the containers are sized to sealingly accommodate the same plungers.

14. A delivery apparatus for delivering orthopaedic material to a medical treatment site, comprising:
    a housing;
    a cartridge removably mounted to said housing;
    a plurality of separate containers for containing said orthopaedic material mounted in said cartridge, said cartridge being removable for replacement with a cartridge with containers having a fresh supply of orthopaedic material;
    a dispensing outlet;
    means for bringing each container into communication with said outlet; and
    means for transferring the orthopaedic material from the containers and through said outlet; and wherein said containers have a constant cross-sectional area along their length; wherein said outlet is provided at an end portion of a dispensing nozzle, said dispensing nozzle arranged to be axially aligned with at least one of said containers, and wherein said dispensing nozzle has a constant cross-sectional area along its length the same as the cross-sectional area of the plurality of containers with which it is aligned.

15. The delivery apparatus of claim 14, wherein an end of the cartridge is such that the material can be loaded into each container mounted within the cartridge from outside the cartridge.

16. The delivery apparatus of claim 15, wherein said cartridge is adapted to receive a clip on funnel.

17. A delivery apparatus for delivering material to a medical treatment site, comprising:
    a housing;
    a cartridge mounted to said housing;
    a plurality of separate containers for containing said material removably mounted in said cartridge, said containers being removable from said cartridge to provide for containers with a fresh supply of material;
    a dispensing outlet;
    means for bringing each container into communication with said outlet; and
    means for transferring the material from the containers and through said outlet, said means for transferring comprising a plunger mounted within said container, the delivery apparatus comprising an advancement means for advancing a plunger through a container in communication with said outlet; and
    wherein said containers have a constant cross-sectional area along their length; wherein said outlet is provided at an end portion of a dispensing nozzle, said dispensing nozzle arranged to be axially aligned with at least one of said containers, and wherein said dispensing nozzle has a constant cross-sectional area along its length the same as the cross-sectional area of the plurality of containers with which it is aligned.

\* \* \* \* \*